(12) United States Patent
Karcher

(10) Patent No.: US 11,666,473 B1
(45) Date of Patent: Jun. 6, 2023

(54) ARM SLING APPARATUS AND METHOD

(71) Applicant: Myles C. Karcher, Tulsa, OK (US)

(72) Inventor: Myles C. Karcher, Tulsa, OK (US)

(73) Assignee: Myles C. Karcher, Tulsa, OK (US)

( * ) Notice: Subject to any disclaimer, the term of this patent is extended or adjusted under 35 U.S.C. 154(b) by 0 days.

(21) Appl. No.: 17/712,831

(22) Filed: Apr. 4, 2022

(51) Int. Cl.
*A61F 5/37* (2006.01)

(52) U.S. Cl.
CPC ................. *A61F 5/3738* (2013.01)

(58) Field of Classification Search
CPC .... A61F 5/3738; A61F 5/3723; A61F 5/3746; A61F 5/3753; A61F 5/37; A61F 5/40
See application file for complete search history.

(56) References Cited

U.S. PATENT DOCUMENTS

| 471,252 | A | 3/1892 | Hanley |
|---|---|---|---|
| 1,121,795 | A | 12/1914 | Burton |
| 4,625,719 | A | 12/1986 | Chambers |
| 5,628,069 | A * | 5/1997 | Ebert ............... A41D 19/01547 2/163 |
| 8,197,429 | B2 | 6/2012 | Neseem |
| D800,326 | S | 10/2017 | Cox |
| 2004/0074257 | A1 | 4/2004 | Weiss et al. |
| 2010/0152635 | A1 | 6/2010 | Borden |
| 2013/0291586 | A1 | 11/2013 | Koeppel |
| 2015/0250638 | A1 | 9/2015 | Howard |

FOREIGN PATENT DOCUMENTS

| DE | 10 2020 108 959 A1 * | 9/2021 |
|---|---|---|
| EP | 1753379 | 6/2004 |

* cited by examiner

*Primary Examiner* — Camtu T Nguyen
(74) *Attorney, Agent, or Firm* — Dennis D. Brown; Brown Patent Law, P.L.L.C.

(57) ABSTRACT

An arm sling apparatus and method in which one or more bistable spring elements in the flexible cover of the arm sling automatically operate to gently clamp and hold the flexible cover in place on the patient's affected arm so that the patient can freely use the patient's other arm and hand to extend and attach the shoulder strap of the arm sling, extend and attach a waste strap of the arm sling if present, and/or perform other tasks necessary for securing the arm sling.

20 Claims, 4 Drawing Sheets

ARM SLING APPARATUS AND METHOD

FIELD OF THE INVENTION

The present invention relates to an arm sling apparatus for immobilizing the arm and/or shoulder of a patient, and to a method of securing an arm sling apparatus on a patient.

BACKGROUND OF THE INVENTION

Arm slings are commonly used for immobilizing a patient's arm or shoulder when needed to prevent further injury or promote healing and recovery following surgery, or in cases where the patient has suffered a fracture, dislocation, or other injury. An arm sling will typically comprise a flexible cover, in which the forearm of the patient is received, and a shoulder strap. After the patient's forearm has been placed in the cover, the shoulder strap must typically be extended over the patient's shoulder and secured to or through a pair of loops, rings, or other attachments on opposite sides of the flexible cover at or near the patient's wrist. In many cases, the arm sling will also include a strap which must be secured around the patient's waste.

Unfortunately, because the patient is only able to use the patient's other arm and hand when securing the arm sling in proper position to immobilize the affected arm or shoulder, it can be difficult for the patient to secure the arm sling without assistance, and/or without causing some movement of the affected arm or shoulder which may be harmful. In particular, it can be especially difficult for the patient to maintain the cover in proper position on the patient's forearm, or prevent the cover from falling off, while the patient must use the patient's only available arm and hand to extend the shoulder strap over the patient's shoulder from back to front and then attach or secure the end of the shoulder strap to or through the loops, rings, or other attachments on opposite sides of the forward end of the flexible cover.

Consequently, a need exists for an improved arm sling, and an improved method for securing the arm sling on a patient, wherein when the forearm of the patient is placed in the flexible cover of the arm sling, the cover will automatically hold itself in place around the patient's forearm and/or wrist and will remain in place while the patient uses the patient's other arm and hand to secure the shoulder strap, and to also secure a waste strap of the arm sling apparatus if present.

SUMMARY OF THE INVENTION

The present invention provides an improved arm sling apparatus and an improved method of securing the arm sling apparatus on a patient. The inventive arm sling apparatus and method satisfy the needs and alleviate the problems discussed above. In the inventive arm sling apparatus and method, when the patient places the patient's forearm in the cover of the arm sling, the cover of the arm sling automatically, and gently, clamps itself around the patient's forearm so that the cover holds itself in proper position and will not fall off of the forearm of the patient while the patient uses the patient's other arm and hand to extend and attach the shoulder strap of the arm sling apparatus, and to also extend and attach a waste strap of the arm sling apparatus if present.

In one aspect, there is provided an arm sling which preferably comprises a flexible cover and a bistable spring element. The flexible cover preferably has a closed rearward longitudinal end which receives an elbow of a patient, an open forward longitudinal end, and a forearm segment which receives a forearm of the patient. The forearm segment extends longitudinally from the closed rearward longitudinal end to the open forward longitudinal end of the flexible cover and the forearm segment preferably has (i) an open top, (ii) a foldable outer side having a longitudinally extending upper border at the open top of the forearm segment, and (iii) a foldable inner side having a longitudinally extending upper border at the open top of the forearm segment.

The bistable stable spring element of the arm sling extends laterally on and/or in the forearm segment of the flexible cover. The bistable spring element preferably has (a) a first end portion which extends on and/or in the foldable outer side of the forearm segment of the flexible cover toward and/or to the longitudinally extending upper border of the foldable outer side of the forearm segment of the flexible cover and (b) a second end portion, opposite the first end portion, which extends on and/or in the foldable inner side of the forearm segment of the flexible cover toward and/or to the longitudinally extending upper border of the foldable inner side of the forearm segment. When the forearm of the patient is placed in the forearm segment of the flexible cover, the bistable spring element is deformable to activate the bistable spring element to move toward a coiled orientation of the bistable spring element which automatically (i) folds the longitudinally extending upper border of the foldable outer side of the forearm segment laterally, around the forearm or a wrist of the patient, toward the longitudinally extending upper border of the foldable inner side of the forearm segment and (ii) folds the longitudinally extending upper border of the foldable inner side of the forearm segment laterally, around the forearm or the wrist of the patient, toward the longitudinally extending upper border of the foldable outer side of the forearm segment.

In another aspect, there is provided a method of placing an arm sling on a patient. The method preferably comprises the step of placing a forearm of the patient in a flexible cover of the arm sling, wherein the flexible cover preferably comprises a reward longitudinal end in which an elbow of the patient is received, an open forward longitudinal end, and a forearm segment which receives the forearm of the patient. The forearm segment of the flexible cover extends longitudinally from the rearward longitudinal end to the open forward longitudinal end of the flexible cover and the forearm segment preferably has (i) an open top, (ii) a foldable outer side having a longitudinally extending upper border at the open top of the forearm segment, and (iii) a foldable inner side having a longitudinally extending upper border at the open top of the forearm segment. In addition, the arm sling preferably also comprises a bistable spring element which extends laterally on and/or in the forearm segment of the flexible cover, the bistable spring element having a first end portion which extends on and/or in the foldable outer side of the forearm segment of the flexible cover toward and/or to the longitudinally extending upper border of the foldable outer side of the forearm segment and a second end portion, opposite the first end portion, which extends on and/or in the foldable inner side of the forearm segment of the flexible cover toward and/or to the longitudinally extending upper border of the foldable inner side of the forearm segment.

After the forearm of the patient is placed in the flexible cover, the method of placing the arm sling on the patient preferably also comprises the step of deforming the bistable spring element to activate the bistable spring element to move toward a coiled orientation of the bistable spring element to automatically (i) fold the longitudinally extending upper border of the foldable outer side of the forearm segment laterally, around the forearm or a wrist of the patient, toward the longitudinally extending upper border of the foldable inner side of the forearm segment and (ii) fold the longitudinally extending upper border of the foldable inner side of the forearm segment laterally, around the forearm or the wrist of the patient, toward the longitudinally extending upper border of the foldable outer side of the forearm segment.

Further aspects, features, and advantages of the present invention will be apparent to those in the art upon examining the accompanying drawings and upon reading the following Detailed Description of the Preferred Embodiments.

DETAILED DESCRIPTION OF THE PREFERRED EMBODIMENTS

Figure 1:
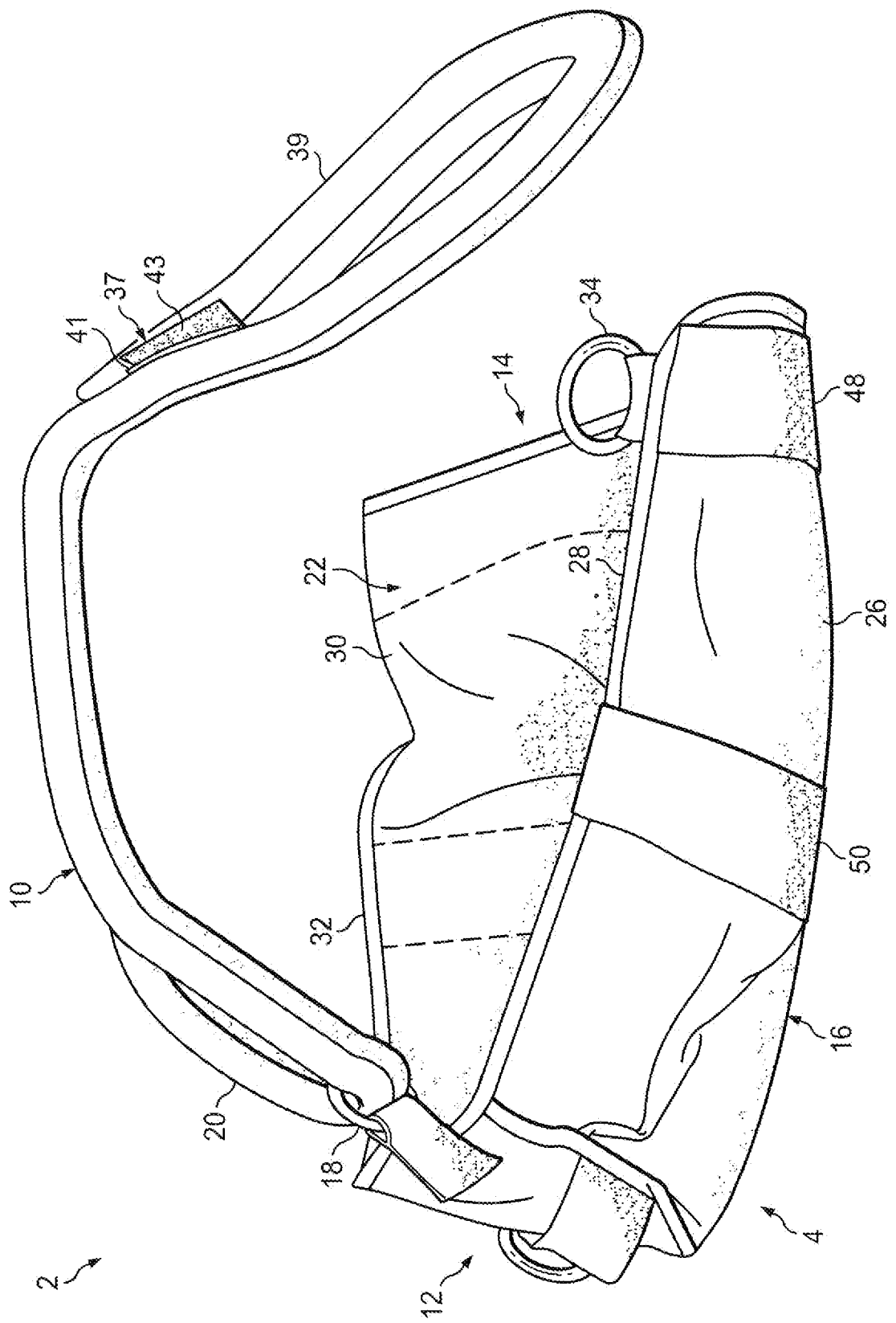
FIG. 1 is a side view of an embodiment 2 of the arm sling provided by the present invention.
Figure 2:
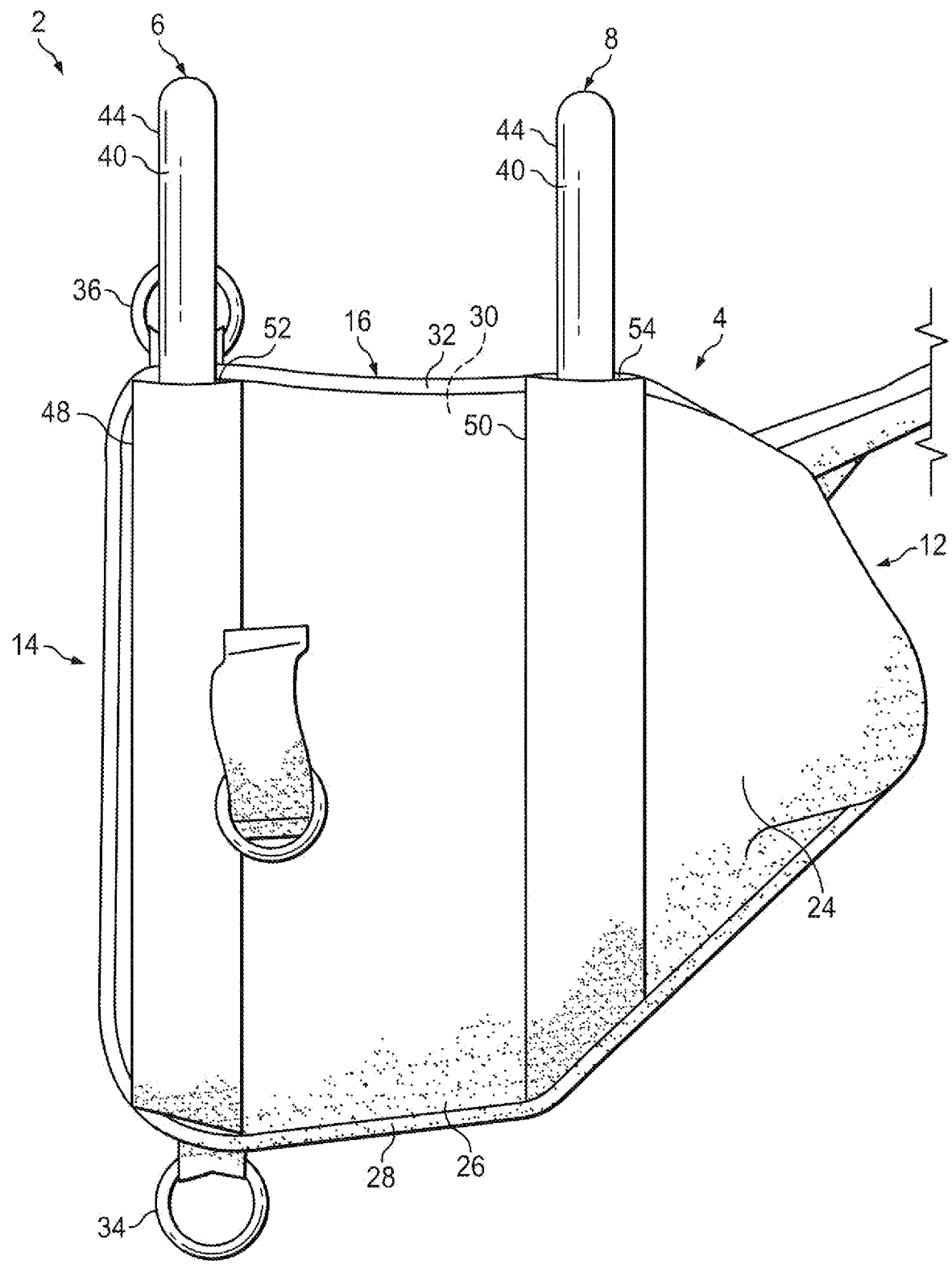
FIG. 2 is a bottom view of the inventive arm sling 2.
Figure 3:
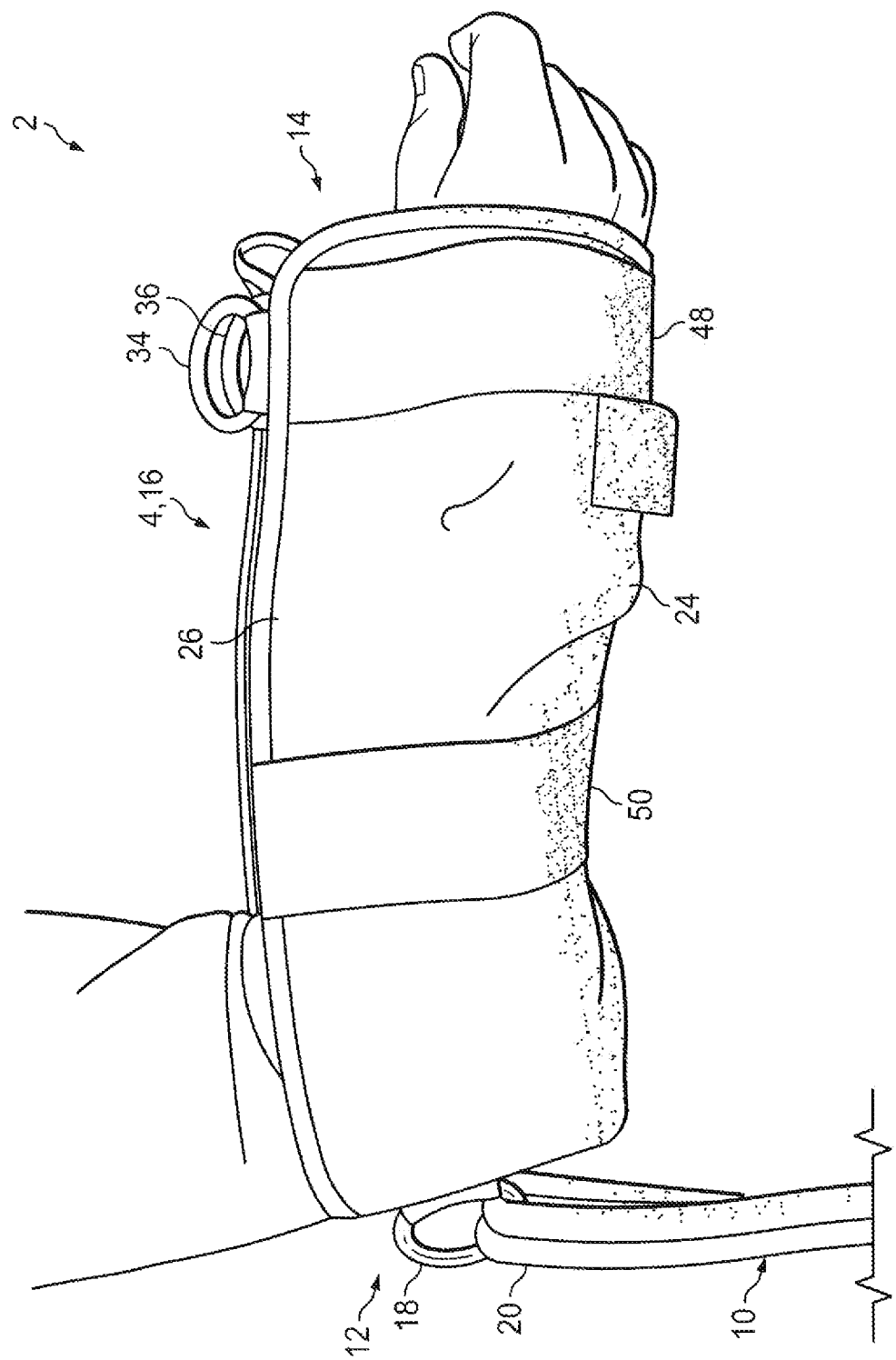
FIG. 3 is another side view of the inventive arm sling 2.
Figure 4:
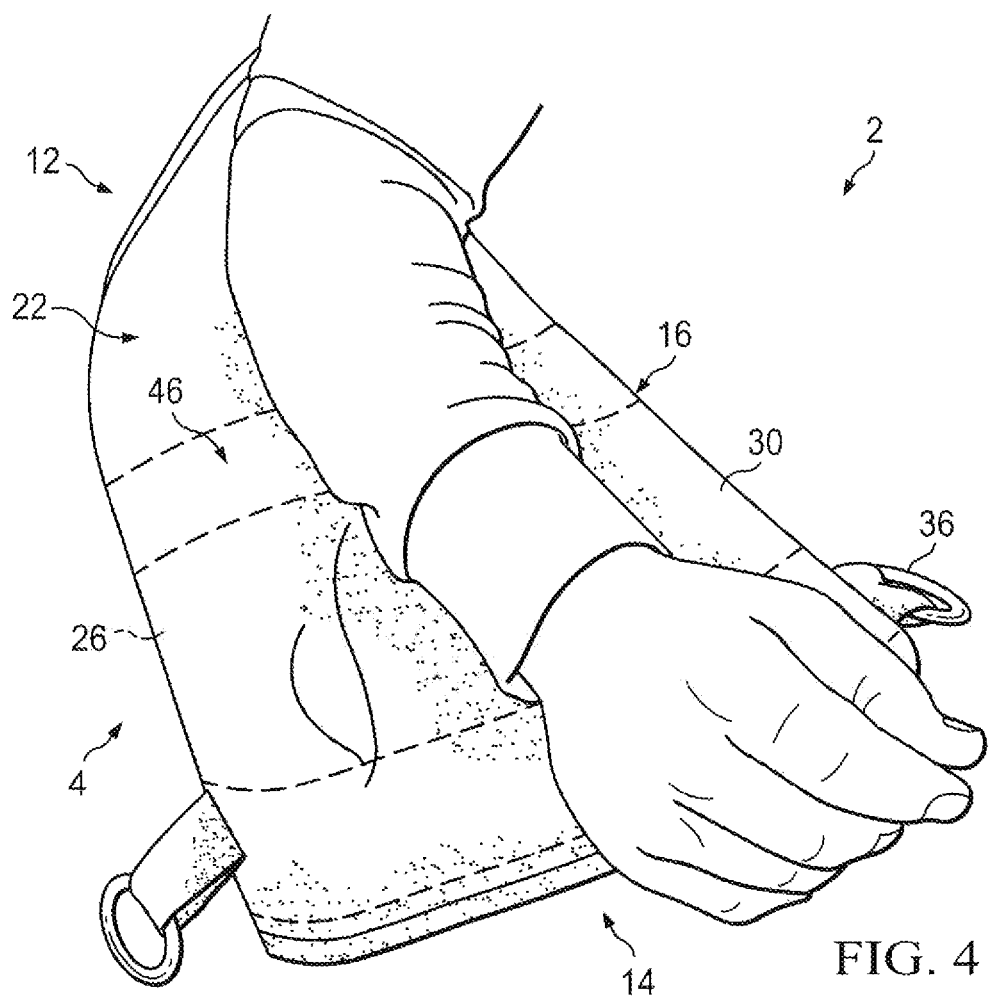
FIG. 4 is a top view of the inventive arm sling 2.
Figure 5:
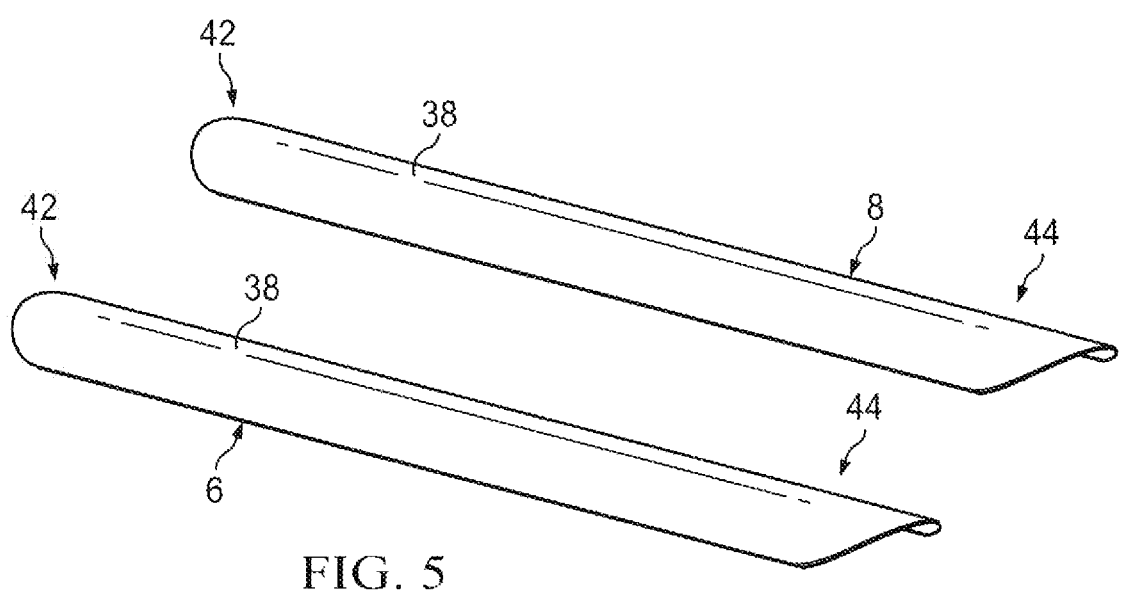
FIG. 5 is a perspective view of a pair of bistable spring elements 6 and 8 used in the inventive arm sling 2.

An embodiment 2 of the arm sling provided by the present invention is illustrated in FIGS. 1-5. The inventive arm sling 2 preferably comprises: a flexible cover 4 for receiving the forearm and elbow of the patient; one or more (preferably two) bistable spring elements 6 and 8 which can be removably or permanently positioned on and/or in the flexible cover 4; and a shoulder strap 10. The inventive arm sling 2 can also include a waste band (not shown) or other features that are commonly used in arm sling apparatuses.

The flexible cover 4 can be formed of an any foldable synthetic, natural, plastic, or other fabric or material which is used in the art for forming arm slings or other medical or orthopedic devices or coverings. The flexible cover 4 preferably comprises: (i) a rearward longitudinal end 12, which will typically be closed, in which the elbow of the patient is received: (ii) an open forward longitudinal end 14 through which the patient's hand, or at least a portion thereof, will typically extend; (iii) a forearm segment 16 in which the forearm of the patient is received; and (iv) a loop, ring, or other attachment 18 provided at or near the rearward end 12 of the flexible cover 4 for securing a proximal end 20 of the shoulder strap 10.

The forearm segment 16 of the flexible cover 4 extends longitudinally from the rearward longitudinal end 12 to the open forward longitudinal end 14 of the flexible cover 4. The forearm segment 16 of the flexible cover 4 preferably comprises: (a) an open top 22 which extends longitudinally from the rearward end 12 to the open forward end 14 of the flexible cover 4; (b) a closed bottom 24 which also extends longitudinally from the rearward end 14 to the open forward end 14 of the flexible cover 4; (c) a foldable outer side 26 of the flexible cover 4 which extends longitudinally from the rearward end 12 to the open forward end 14 of the flexible cover 4 and extends upwardly from the closed bottom 24 to the open top 22 of the forearm segment 16; (d) a longitudinally extending upper border 28 of the foldable outer side 26 of the flexible cover 4 which is located at the open top 22 of the forearm segment 16; (e) a foldable inner side 30 of the flexible cover 4 which extends longitudinally from the rearward end 12 to open forward end 14 of the flexible cover 4 and extends upwardly from the closed bottom 24 to the open top 22 of the forearm segment 16; (f) a longitudinally extending upper border 32 of the foldable inner side 30 of the flexible cover 4 which is located at the open top 22 of the forearm segment 16; (g) a loop, ring, or other attachment 34 for the shoulder strap 10 which is provided on the upper border 28 or elsewhere on a forward portion of the foldable outer side 26 of the forearm segment 16; and (h) a loop, ring, or other attachment 36 for the shoulder strap 10 which is provided on the upper border 32 or elsewhere on a forward portion of the foldable inner side 30 of the forearm segment 16.

The shoulder strap 10 can have any type of attachment 37 on the distal end or distal end portion 39 thereof which is suitable for attaching to the loops, rings, or other attachments 34 and 36 provided at or near the forward ends of the foldable outer and inner sides 26 and 30 of the flexible cover 4. The forward attachments 34 and 36 on the foldable outer and inner sides 26 and 30 of the flexible cover 4 will preferably be loops or rings. The attachment 37 on the distal end portion 39 of the shoulder strap 10 will preferably be a hook and loop (e.g., Velcro) attachment comprising a rearward element (e.g., a loop pad) 41 which is spaced apart from a forward element (e.g., a hook pad) 43 such that the forward element 43 on the shoulder strap 10 can be inserted through the each of the two loops or rings 34 and 36 at the forward end of the flexible cover 4 and then doubled back into attachment with the rearward element 41.

Each of the one or more bistable spring elements 6 and 8 used in the inventive arm sling can generally be any type of band which (a) can be straightened from a stable coiled orientation to a stable elongate linear orientation and (b) will spring back to the stable coiled orientation when the straightened linear band is pressed or when some other deforming force is applied to the straightened band. The one or more bistable spring elements 6 and 8 can be formed of metal, plastic, or any other material effective for providing the above-describe bistable straightening and coiling characteristics. The one or more bistable spring elements 6 and 8 will preferably be formed of stainless steel or other material of the type used for forming bistable slap bracelets or bistable self-retracting tape measures. One or both sides of each of the bistable spring elements 6 and 8 can also be covered or coated with one or more layers of fabric, plastic, leather, or other material such as commonly used, e.g., on slap bracelets. Most preferably, each of the one or more bistable spring elements 6 and 8 will be a slap bracelet.

In its straightened, elongate linear orientation, each of the one or more bistable spring elements 6 and 8 preferably has an arced cross-sectional shape which extends along the entire length of the straightened linear band 6 and/or 8. Because of the arced, cross-section shape of the one or more bistable bands 6 and 8 when in the straightened linear orientation, each of the straightened linear bands 6 and/or 8 has (i) a convex (outwardly curved) side 38 which extends along the length of the straightened band 6 or 8 and (ii) an opposite concave (inwardly curved) side 40 which also extends along the length of the straightened band 6 or 8. When the straightened linear band 6 or 8 is deformed, e.g., by applying a pressing force to the convex (outwardly curved) side 38 of the straightened band 6 or 8, the straightened band 6 or 8 will automatically spring to, or at least toward, the stable coiled orientation of the band 6 or 8.

Each of the one or more bistable spring elements 6 and 8 extends laterally (transversely) on and/or in the forearm segment 16 of the flexible cover 4 and is preferably positioned to wrap around the forearm or the wrist of the patient. The length of each of the one or more bistable spring elements 6 and 8 is preferably less than or equal to the lateral width of the forearm segment 16 such that (a) a first end portion 42 of the bistable spring element 6 or 8 will extend on and/or in the foldable outer side 26 of the forearm segment 16 toward and/or to the longitudinally extending upper border 28 of the foldable outer side 26 of the forearm segment 16 and (b) a second end portion 44 of the bistable spring element 6 or 8, opposite the first end portion 42, will extend on and/or in the foldable inner side 30 of the forearm segment 16 toward and/or to the longitudinally extending upper border 32 of the foldable inner side 30 of the forearm segment 16.

Before placing the patient's forearm in the flexible cover 4 of the inventive arm sling 2, each of the bistable spring elements 6 and/or 8 will preferably be straightened to extend laterally on and/or in the forearm segment 16 of the flexible cover 2 in its straightened linear orientation with the concave side 40 of the straightened spring element 6 and/or 8 facing outwardly and the convex side 38 of the straightened spring element 6 and/or 8 facing the interior portion 46 of the flexible cover 4 in which the forearm of the patient will be received.

When the patient's forearm is then placed in the forearm segment 16 of the flexible cover 4, each of the one or more bistable spring elements 6 and 8 can be deformed, e.g., by pressing the convex side 38 of each straightened spring element 6 and/or 8 against the patient's forearm or wrist or by other means, such that the bistable spring element 6 and/or 8 is automatically activated to spring from its stable linear orientation toward its coiled orientation. As the one or more bistable spring elements 6 and 8 spring from the straightened orientation toward the coiled orientation, the one or more bistable spring elements 6 and 8 automatically act to (i) fold the longitudinally extending upper border 28 of the foldable outer side 26 of the forearm segment 16 laterally, around the forearm or a wrist of the patient, toward the longitudinally extending upper border 32 of the foldable inner side 30 of the forearm segment 16 and (ii) fold the longitudinally extending upper border 32 of the foldable inner side 30 of the forearm segment 16 laterally, around the forearm or the wrist of the patient, toward the longitudinally extending upper border 28 of the foldable outer side 26 of the forearm segment 16.

Each of the one or more bistable spring elements 6 and 8 will preferably be positioned in a laterally (transversely) extending sleeve 48 or 50 which is provided on or in the forearm segment 16 of the flexible cover 4. Each of the one or more sleeves 48 and 50 will preferably be sewn on or otherwise attached to the exterior of the forearm segment 16 of the flexible cover 4. In addition, each of the one or more sleeves 48 and 50 will preferably have an open end 52 or 54 for removably inserting the one or more bistable spring elements 6 and 8 so that the one or more bistable spring elements 6 and 8 can be removed for washing the flexible cover 4 or for other purposes.

The inventive arm sling 2 preferably comprises a first bistable spring element 6 and a second bistable spring element 8. The first bistable spring element 6 is preferably positioned and/or removably inserted in a first sleeve 48 which extends laterally (transversely) across a forward end portion of the forearm segment 16 of the flexible cover 2 at or near the location of the patient's wrist. The second bistable spring element 8 is preferably positioned and/or removably inserted in a second sleeve 50 which extends laterally across the forearm segment 16 of the flexible cover 2 at a location which is longitudinally between the first sleeve 48 and the rearward longitudinal end 12 of the flexible cover 4.

In the method of the present invention using the inventive arm sling 2, each of the one or more bistable spring elements 6 and/or 8 of the arm sling 2 is inserted into the corresponding laterally extending sleeve(s) 48 and/or 50 provided on and/or in the forearm segment 16 of the flexible cover 4. Also, if in the coiled orientation, each of the one or more bistable spring elements 6 and/or 8 will be straightened from the coiled state to its linear orientation.

Next, the patient places the forearm and elbow of the patient's affected arm in the interior 46 of the flexible cover 4 and then deforms each of the one or more straightened spring elements 6 and/or 8 by, e.g., pressing the one or more straightened elements 6 and/or 8 against the forearm or wrist of the affected arm. This deformation of the one or more bistable spring elements 6 and/or 8 activates each bistable spring elements 6 and/or 8 to move/spring toward the coiled orientation of the bistable spring element 6 and/or 8.

As the bistable spring element(s) 6 and/or 8 spring(s) to toward the coiled orientation, each of the one or more bistable spring elements operates to automatically (i) fold the longitudinally extending upper border 28 of the foldable outer side 26 of the forearm segment 16 of the flexible cover 4 laterally, around the forearm or a wrist of the patient, toward the longitudinally extending upper border 32 of the foldable inner side 30 of the forearm segment 16 and (ii) fold the longitudinally extending upper border 32 of the foldable inner side 30 of the forearm segment 16 laterally, around the forearm or the wrist of the patient, toward the longitudinally extending upper border 28 of the foldable outer side 26 of the forearm segment 16.

As a result, the one or more bistable spring elements 6 and/or 8 gently clamp and hold the flexible cover 4 in place on the patient's forearm while the patient uses the patient's other arm and hand to grasp the distal end portion 39 of the shoulder strap 10, extend the shoulder strap 10 over the patient's shoulder from back to front, and then attach the distal end or end portion 39 of the shoulder strap 10 to the forward attachment loops or rings 34 and 36 of the flexible cover 4 by, e.g., inserting a forward element 43 of a hook and loop attachment 37 on the distal end portion 39 of the shoulder strap 10 through each of the two loops or rings 34 and 36 at the forward end of the flexible cover 4 and then doubling the forward attachment element 43 back into attachment with the rearward element 41 of the hook and loop attachment 37.

Thus, the present invention is well adapted to carry out the objects and attain the ends and advantages mentioned above as well as those inherent therein. While presently preferred embodiments have been described for purposes of this disclosure, numerous changes and modifications will be apparent to those in the art. Such changes and modifications are encompassed within this invention as called for by the claims.

What is claimed is:

1. An arm sling comprising:
   a flexible cover having
      a closed rearward longitudinal end configured to receive an elbow of a patient,
      an open forward longitudinal end, and
      a forearm segment configured to receive a forearm of the patient, the forearm segment extending longitudinally from the closed rearward longitudinal end to the open forward longitudinal end of the flexible cover and the forearm segment having (i) an open top, (ii) a foldable outer side having a longitudinally extending upper border at the open top of the forearm segment, and (iii) a foldable inner side having a longitudinally extending upper border at the open top of the forearm segment;

a bistable spring element which extends laterally on and/or in the forearm segment of the flexible cover, the bistable spring element having (a) a first end portion which extends on and/or in the foldable outer side of the forearm segment of the flexible cover toward and/or to the longitudinally extending upper border of the foldable outer side of the forearm segment and (b) a second end portion, opposite the first end portion, which extends on and/or in the foldable inner side of the forearm segment of the flexible cover toward and/or to the longitudinally extending upper border of the foldable inner side of the forearm segment; and the bistable spring element being deformable when the forearm of the patient is in the forearm segment of the flexible cover to activate the bistable spring element to move toward a coiled orientation of the bistable spring element which automatically (i) folds the longitudinally extending upper border of the foldable outer side of the forearm segment laterally, around the forearm or a wrist of the patient, toward the longitudinally extending upper border of the foldable inner side of the forearm segment and (ii) folds the longitudinally extending upper border of the foldable inner side of the forearm segment laterally, around the forearm or the wrist of the patient, toward the longitudinally extending upper border of the foldable outer side of the forearm segment.

2. The arm sling of claim 1 further comprising the bistable spring element being a slap bracelet.

3. The arm sling of claim 1 further comprising the bistable spring element comprising a stainless steel bistable spring band.

4. The arm sling of claim 1 further comprising the bistable spring element being positioned in a laterally extending sleeve provided on or in the forearm segment of the flexible cover.

5. The arm sling of claim 4 further comprising the laterally extending sleeve having an open end for removably inserting the bistable spring element in the laterally extending sleeve.

6. The arm sling of claim 1 further comprising:
the bistable spring element being a first bistable spring element;
the arm sling also comprising a second bistable spring element which extends laterally on and/or in the forearm segment of the flexible cover, the second bistable spring element being positioned longitudinally between the first bistable spring element and the closed rearward longitudinal end of the flexible cover and the second bistable spring element having (a) a first end portion which extends on and/or in the foldable outer side of the forearm segment of the flexible cover toward and/or to the longitudinally extending upper border of the foldable outer side of the forearm segment and (b) a second end portion, opposite the first end portion of the second bistable spring element, which extends on and/or in the foldable inner side of the forearm segment of the flexible cover toward and/or to the longitudinally extending upper border of the foldable inner side of the forearm segment; and the second bistable spring element being deformable when the forearm of the patient is in the forearm segment of the flexible cover to activate the second bistable spring element to move toward a coiled orientation of the second bistable spring element which automatically (i) folds the longitudinally extending upper border of the foldable outer side of the forearm segment laterally, around the forearm of the patient, toward the longitudinally extending upper border of the foldable inner side of the forearm segment and (ii) folds the longitudinally extending upper border of the foldable inner side of the forearm segment laterally, around the forearm of the patient, toward the longitudinally extending upper border of the outer side of the forearm segment.

7. The arm sling of claim 6 further comprising each of the first and the second bistable spring elements being a slap bracelet.

8. The arm sling of claim 6 further comprising each of the first and the second bistable spring elements comprising a stainless steel bistable spring band.

9. The arm sling of claim 6 further comprising:
the first bistable spring element being positioned in a first laterally extending sleeve provided on or in the forearm segment of the flexible cover;
the second bistable spring element being positioned in a second laterally extending sleeve provided on or in the forearm segment of the flexible cover, the second laterally extending sleeve being positioned longitudinally between the first laterally extending sleeve and the closed rearward longitudinal end of the flexible cover;
the first laterally extending sleeve having an open end for removably inserting the first bistable spring element in the first laterally extending sleeve; and
the second laterally extending sleeve having an open end for removably inserting the second bistable spring element in the second laterally extending sleeve.

10. The arm sling of claim 1 further comprising a shoulder strap which extends from the closed rearward longitudinal end of the flexible cover and has a distal end or a distal end segment which is securable to both (i) an attachment provided on a forward end portion of the foldable outer side of the forearm segment of the flexible cover and (ii) an attachment provided on a forward end portion of the foldable inner side of the forearm segment of the flexible cover.

11. A method of placing an arm sling on a patient comprising the steps of:
a) placing a forearm of the patient in a flexible cover of the arm sling, the flexible cover comprising a reward longitudinal end in which an elbow of the patient is received, an open forward longitudinal end, and a forearm segment which receives the forearm of the patient, the forearm segment extending longitudinally from the rearward longitudinal end to the open forward longitudinal end of the flexible cover and the forearm segment having (i) an open top, (ii) a foldable outer side having a longitudinally extending upper border at the open top of the forearm segment, and (iii) a foldable inner side having a longitudinally extending upper border at the open top of the forearm segment, the arm sling also comprising a bistable spring element which extends laterally on and/or in the forearm segment of the flexible cover, the bistable spring element having a first end portion which extends on and/or in the foldable outer side of the forearm segment of the flexible cover toward and/or to the longitudinally extending upper border of the foldable outer side of the forearm segment and a second end portion, opposite the first end portion, which extends on and/or in the flexible inner side of the forearm segment of the flexible cover toward and/or to the longitudinally extending upper border of the foldable inner side of the forearm segment and then b) deforming the bistable spring element to activate the bistable spring element to move toward a coiled orientation of the bistable spring element to automatically (i) fold the longitudinally extending upper border of the foldable outer side of the forearm segment laterally, around the forearm or a wrist of the patient, toward the longitudinally extending upper border of the foldable inner side of the forearm segment and (ii) fold the longitudinally extending upper border of the foldable inner side of the forearm segment laterally, around the forearm or the wrist of the patient, toward the longitudinally extending upper border of the foldable outer side of the forearm segment.

12. The method of claim 11 further comprising the bistable spring element being a slap bracelet.

13. The method of claim 11 further comprising the bistable spring element comprising a stainless steel bistable spring band.

14. The method of claim 11 further comprising the step, prior to step (a), of inserting the bistable spring element in a laterally extending sleeve provided on or in the forearm segment of the flexible cover.

15. The method of claim 11 further comprising:
the bistable spring element being a first bistable spring element;
the arm sling also comprising a second bistable spring element which extends laterally on and/or in the forearm segment of the flexible cover, the second bistable spring element being positioned longitudinally between the first bistable spring element and the rearward longitudinal end of the flexible cover and the second bistable spring element having (i) a first end portion which extends on and/or in the foldable outer side of the forearm segment of the flexible cover toward and/or to the longitudinally extending upper border of the foldable outer side of the forearm segment and (ii) a second end portion, opposite the first end portion of the second bistable spring element, which extends on and/or in the foldable inner side of the forearm segment of the flexible cover toward and/or to the longitudinally extending upper border of the foldable inner side of the forearm segment; and
the method further comprising the step, after step (a), of deforming the second bistable spring element to activate the second bistable spring element to move toward a coiled orientation of the second bistable spring element to automatically (i) fold the longitudinally extending upper border of the foldable outer side of the forearm segment laterally, around the forearm of the patient, toward the longitudinally extending upper border of the foldable inner side of the forearm segment and (ii) fold the longitudinally extending upper border of the foldable inner side of the forearm segment laterally, around the forearm of the patient, toward the longitudinally extending upper border of the foldable outer side of the forearm segment.

16. The method of claim 15 further comprising each of the first and the second bistable spring elements being a slap bracelet.

17. The method of claim 15 further comprising each of the first and the second bistable spring elements comprising a stainless steel bistable spring band.

18. The method of claim 15 further comprising the steps, prior to step (a), of:
inserting the first bistable spring element in a first laterally extending sleeve provided on or in the forearm segment of the flexible cover and
inserting the second bistable spring element in a second laterally extending sleeve provided on or in the forearm segment of the flexible cover, the second laterally extending sleeve being positioned longitudinally between the first laterally extending sleeve and the rearward longitudinal end of the flexible cover.

19. The method of claim 11 further comprising the steps, after step (b), of:
extending a shoulder strap from the rearward longitudinal end of the flexible cover over a shoulder of the patient and
securing a distal end or a distal end segment of the shoulder strap to both (i) a first attachment provided on a forward end portion of the foldable outer side of the forearm segment of the flexible cover and (ii) a second attachment provided on a forward end portion of the foldable inner side of the forearm segment of the flexible cover.

20. The method of claim 19 further comprising:
the first attachment being a first attachment loop or ring;
the second attachment being a second attachment loop or ring;
the distal end segment of the shoulder strap having a hook element and a loop element of a hook and loop attachment thereon; and
the step of securing comprising extending the distal end of the shoulder strap through both the first attachment loop or ring and the second attachment loop or ring and attaching the hook element to the loop element of the hook and loop attachment.

* * * * *